United States Patent [19]

Raad et al.

[11] Patent Number: 5,217,493

[45] Date of Patent: Jun. 8, 1993

[54] ANTIBACTERIAL COATED MEDICAL IMPLANTS

[75] Inventors: Issam I. Raad; Rabih O. Darouiche, both of Houston, Tex.

[73] Assignee: Board of Regents, The University of Texas System, Austin, Tex.

[21] Appl. No.: 850,197

[22] Filed: Mar. 11, 1992

[51] Int. Cl.$^5$ ............................................. A61F 2/02
[52] U.S. Cl. ..................................... 623/11; 604/265
[58] Field of Search ....................... 623/1, 66; 604/265, 604/266, 890.1; 427/2

[56] References Cited

U.S. PATENT DOCUMENTS

| | | |
|---|---|---|
| 4,107,121 | 8/1978 | Stoy . |
| 4,678,660 | 7/1987 | McGary et al. . |
| 4,749,585 | 6/1988 | Greco et al. . |
| 4,846,844 | 7/1987 | DeLeon et al. ............... 623/66 |
| 4,879,135 | 11/1989 | Greco et al. ................. 623/1 |
| 4,895,566 | 1/1990 | Lee . |
| 4,915,694 | 4/1990 | Yamamoto et al. . |
| 4,917,686 | 4/1990 | Bayston et al. . |
| 4,952,419 | 8/1990 | DeLeon et al. . |
| 5,013,306 | 5/1991 | Solomon et al. . |

OTHER PUBLICATIONS

Raad et al., 31st Interscience Conference on Antimicrobial Agents and Chemotherapy, Abstract No. 31, (Sep. 29, 1991).

Darouiche et al., "Eradication of Colonization by Methicillin-Resistant *Staphylococcus aureus* by Using Oral Minocycline-Rifampin and Topical Mupirocin", Antimicrobial Agents and Chemotherapy 35:1612–1615 (Aug. 1991).

Kamal et al., "Reduced Intravascular Catheter Infection by Antibiotic Bonding", Journal of American Medical Association 265:2364–2368 (May 8, 1991).

Raad et al., "Alternative Agents Against Staphylococcal Isolates Causing Catheter Related Bacteremia (CRB) in Cancer Patients", 90th Annual Meeting of the American Society for Microbiology, Abstract No. A149 (May 13, 1990).

Farber et al., "*Staphylococcus epidermidis* Extracted Slime Inhibits the Antimicrobial Action of Clycopeptide Antibiotics", Journal of Infectious Diseases 161:37–40 (1990).

Segreti et al., "In Vitro Activity of Minocycline and Rifampin Against Staphylococci", Diagn. Microbiol. Infect. Dis. 12:253–255 (1989).

Sherertz et al., "Efficacy of Dicloxacillin-Coated Polyurethane Catheters in Preventing Subcutaneous *Staphylococcus aureus* Infection in Mice", Antimicrobial Agents and Chemotherapy 33:1174–1178 (Aug. 1989).

Evans et al., "Effect of Vancomycin Hydrochloride on *Staphylococcus epidermidis* Biofilm Associated with Silicone Elastomer", Antimicrobial Agents and Chemotherapy 31:889–894 (Jun. 1987).

Yourassowsky et al., "Combination of Minocycline and Rifampicin Against Methicillin-and Gentamicin-Resistant *Staphylococcus aureus*, ", Journal of Clinical Pathology 34:559–563 (1981).

Zinner et al., "Antistaphylococcal Acivity of Rifampin with Other Antibiotics", Journal of Infectious Diseases 144:365–371 (Oct. 1981).

*Primary Examiner*—David Isabella
*Attorney, Agent, or Firm*—Arnold, White & Durkee

[57] ABSTRACT

An implantable medical device having long lasting resistance to staphylococcal biofilm colonization is provided. Implantable medical devices such as catheters, shunts, prosthesis, pacemakers, etc. are susceptible to colonization by biofilm adherent microorganisms, especially staphylococci. While systemic staphylococcal infections are effectively treated by many antibiotics, vancomycin being the antibiotic of choice, this same bacteria when encased in biofilm adhering to indwelling medical devices is generally resistant to antibiotic treatment. By the present invention, the combination of rifampin and minocycline or the combination of rifampin and novobiocin when coated on the surfaces of implantable medical devices unexpectedly provides superior antibacterial activity against staphylococcal biofilm colonization on the coated surface of indwelling medical devices.

12 Claims, No Drawings

ANTIBACTERIAL COATED MEDICAL IMPLANTS

FIELD OF THE INVENTION

The present invention relates to indwelling medical articles, such as catheters, coated with antibiotics to inhibit bacterial growth.

BACKGROUND OF THE INVENTION

Indwelling medical devices including vascular catheters are becoming essential in the management of hospitalized patients by providing venous access. The benefit derived from these catheters as well as other types of catheters such as peritoneal catheters, cardiovascular, orthopedic and other prosthetic devices is often upset by infectious complications. The most common organisms causing these infectious complications are *Staphylococcus epidermidis* and *Staphylococcus aureus*. In the case of vascular catheters, these two organisms account for almost 70-80% of all infectious organisms, with *Staphylococcus epidermidis* being the most common organism. *Candida albicans*, a fungal agent, account for about 10-15% of catheter infections.

Colonization of bacteria on the interior surfaces of the catheter or other part of the device can produce serious patient problems, including the need to remove and/or replace the implanted device and to vigorously treat secondary infective conditions. A considerable amount of attention and study has been directed toward preventing such colonization by the use of antimicrobial agents, such as antibiotics, bound to the surface of the materials employed in such devices. In such attempts the objective has been to produce a sufficient bacteriostatic or bactericidal action to prevent colonization.

Vancomycin was thought to be the logical antibiotic to use since it is the antibiotic of choice to treat systemic staphylococcal infections, particularly methicillin resistant *S. epidermidis* and *S. aureus*. However, vancomycin has several limitations:

(a) While several investigators have shown that vancomycin is active against nonadherent staphylococci in vitro and human tissue, it is not active against the staphylococci that adhere to foreign bodies and embed themselves in a layer of biofilm. The biofilm (slime or fibrous glycocalix) not only acts as a shield protecting the adherent staphylococci from vancomycin, but also inhibits the activity of glycopeptide antibiotics (vancomycin and teicoplanin). See e.g. Farber et al. *J. Infect. Dis.* 161:37-40 (1990); and Evans et al., *Antimicrob. Agents Chemother.* 31:889-894 (1987).

(b) Using vancomycin prophylactically on a highly colonized surface (such as a catheter) will lead to the emergence of vancomycin resistant staphylococci, and would deprive the clinician of the only available therapeutic choice (glycopeptide antibiotics such as vancomycin and teicoplanin) should these resistant staphylococci cause bacteremia or deep seated infection.

(c) Vancomycin has no activity on *Candida albicans*; its use would decrease the rate of staphylococcal device related infections at the expense of increasing the more complicated fungal superinfections.

Recent investigations into catheter associated infections have shown that bacterial produced adherent biofilms promote staphylococcal and Pseudomonas tolerance to antibiotics normally effective against the same bacteria systemically or in tissue. A dramatic representation of this problem was demonstrated by the inability of tobramycin to kill *Pseudomas aeruginosa* cells embedded in a biofilm at antibiotic levels of greater than 50 times the minimum bactericidal concentration (MBC) for the identical strain grown in liquid suspension. Nickel et al., *Antimicrob. Agents Chemother.* 27:619-624 (1985). Similarly, six weeks of intensive antibacterial chemotherapy with a $\beta$ lactam antibiotic, to which laboratory cultures were exquisitely sensitive, failed to prevent frequent recurrences of a *S. aureus* bacteremia originating from an endocardial pacemaker. Direct examination of the tip of the pacemaker lead, revealed that the staphylococci grew in phenomenally thick slimed enclosed biofilm which protected the bacteria from very high tissue levels of antibiotic. Subsequent in vitro studies showed the biofilm adherent bacteria were resistant to levels of antibiotics 50 to 100 times higher than the MBC needed to kill nonbiofilm encased cells of the same strain. Khoury, A. E. and Costeron J. W., "Bacterial Biofilms in Nature and Disease," *Dialogues in Pediatric Urology*, Vol. 14:2-5 (1991).

Although a considerable amount of attention and study has been directed toward preventing such colonization by the use of antimicrobial agents coated to indwelling medical devices, the need persists for improved means to combat bacterial colonization of such devices.

SUMMARY OF THE INVENTION

This invention provides antibiotic combinations of (a) rifampin and minocycline or (b) rifampin and novobiocin for coating surfaces of indwelling medical devices. Both of these antibiotic combinations are very effective in killing biofilm-associated staphylococci, particularly *Staphylococcus epidermidis* and *Staphylococcus aureus*, when applied to the surfaces of an indwelling medical device. In particular, these combinations were surprisingly effective in preventing in situ microbial colonization of indwelling medical devices and were superior to any other antibiotic combination in killing biofilm-adherent staphylococcal organisms in situ.

DETAILED DESCRIPTION OF THE PREFERRED EMBODIMENTS

In accordance with the present invention, there is provided an implantable medical device having a portion of its surfaces coated with an antibiotic combination of (a) rifampin and minocycline or (b) rifampin and novobiocin, the combination of antibiotics in an amount sufficient to inhibit growth of biofilm encased bacteria on the coated surface. The antibiotic combination can be applied to the surfaces of the devices in any number of ways, including for example but not limited to, ionic binding to a surface coating, passive adsorption, or dispersion within a polymeric base material making up the surface of the device or coated on the device surfaces.

Rifampin is a semisynthetic derivative of rifamycin B, a macrocyclic antibiotic compound produced by the mold *Streptomyces mediterranic*. Rifampin inhibits bacterial DNA-dependent RNA polymerase activity and is bactericidal in nature. Rifampin is a zwitterion that is soluble in acidic aqueous solutions, is even more soluble in organic solvents, and displays exceptional diffusion through lipids. Rifampin is available in the United States from Merrill Dow Pharmaceuticals, Cincinnati, Ohio.

Minocycline is a semisynthetic antibiotic derived from tetracycline. It is primarily bacteriostatic and exerts its antimicrobial effect by inhibiting protein synthesis. Minocycline is commercially available as the hydrochloride salt which occurs as a yellow, crystalline powder and is soluble in water and slightly soluble in alcohol. Following reconstitution of sterile minocycline hydrochloride with sterile water for injection, solutions have a pH of 2-2.8. Minocycline is available from Lederle Laboratories Division, American Cyanamid Company, Pearl River, N.Y.

Novobiocin is an antibiotic obtained from cultures of *Streptomyces niveus* or *S. spheroides*. Novobiocin is usually bacteriostatic in action and appears to interfere with bacterial cell wall synthesis and inhibits bacterial protein and nucleic acid synthesis. The drug also appears to affect stability of the cell membrane by complexing with magnesium. Novobiocin sodium is freely soluble in water and alcohol. Novobiocin is available from The Upjohn Company, Kalamazoo, Mich.

The amount of each antibiotic used to coat the medical device surfaces varies to some extent with the method of coating application. In general, however, the concentration of each antibiotic can range from about 0.01 mg per $cm^2$ to about 10 mg per $cm^2$.

The medical devices which are amenable to coatings of the subject antibiotic combinations generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings with the antibiotic combinations. Such devices, for example bone and joint prosthesis, can be coated by cement mixture containing the subject antibiotic compounds. During implant use, the antibiotics leach from the cement into the surrounding prosthesis surface environment. Particular devices especially suited for application of the antibiotic combinations of this invention include intravascular, peritoneal, pleural and urological catheters; heart valves; cardiac pacemakers; vascular shunts; and orthopedic, intraocular, or penile prosthesis.

Various methods can be employed to coat the surfaces of medical devices with the antibiotic combination. For example, one of the simplest methods would be to flush the surfaces of the device with a solution of the antibiotic combination. Generally, coating the surfaces by a simple flushing technique would require convenient access to the implantable device. For example, catheters, are generally amenable to flushing with a solution of rifampin and minocycline or rifampin and novobiocin. For use in flushing solutions, the effective concentration of the antibiotic would range from about 1 to 10 $\mu$g/ml for minocycline, preferably about 2 $\mu$g/ml; 1 to 10 $\mu$g/ml for rifampin, preferably about 2 $\mu$g/ml; and 1 to 10 $\mu$g/ml for novobiocin, preferably about 2 $\mu$g/ml. The flushing solution would normally be composed of sterile water or sterile normal saline solutions.

Another method of coating the devices would be to first apply or adsorb to the surface of the medical device a layer of tridodecylmethyl ammonium chloride (TDMAC) surfactant followed by a coating layer of antibiotic combination. For example, a medical device having a polymeric surface, such as polyethylene, silastic elastomers, polytetrafluoroethylene or Darcon, can be soaked in a 5% by weight solution of TDMAC for 30 minutes at room temperature, air dried, and rinsed in water to remove excess TDMAC. Alternatively, TDMAC precoated catheters are commercially available; for example, arterial catheters coated with TDMAC are available from Cook Crtical Care, Bloomington, Ind. The device carrying the absorbed TDMAC surfactant coated can then incubated in a solution of the antibiotic combination for one hour or so, washed in sterile water to remove unbound antibiotic and stored in a sterile package until ready for implantation. In general, the solution of antibiotic combination is composed of a concentration of 0.01 mg/ml to 50 mg/ml, preferably 10 mg/ml of each antibiotic in an aqueous pH 7.4-7.6 buffered solution or sterile water.

Alternative processes and reagents for bonding antibiotics to surfactant coated implantable medical devices are provided in U.S. Pat. Nos. 4,442,133, 4,678,660 and 4,749,585, the entire contents of which are incorporated herein by reference. A further method useful to coat the surface of medical devices with the subject antibiotic combinations involves first coating the selected surfaces with benzalkonium chloride followed by ionic bonding of the antibiotic composition. See, e.g., Solomon, D. D. and Sherertz, R. J., *J. Controlled Release* 6:343-352 (1987) and U.S. Pat. No. 4,442,133.

Other methods of coating surfaces of medical devices with antibiotics are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is adsorbed into the matrix of the surface material of the medical device); U.S. Pat. No. 4,107,121 (constructing the medical device with ionogenic hydrogels, which thereafter sorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

These and many other methods of coating antibiotics to medical devices appear in numerous patents and medical journal articles. As is evident, one of ordinary skill having benefit of this disclosure would be apprised of several different methods of coating various medical device surfaces with the subject inventive antibiotic coatings.

We coated catheter surfaces with different combinations over a two-year period and then exposed the catheter surfaces to clinical staphylococci isolates using a Modified Robbin's Device which simulates a vascular catheter. The combination that stood out was that of rifampin and minocycline. The combination of rifampin and novobiocin also provided unexpectedly superior results in inhibiting colonization of biofilm-associated bacteria on the surface of indwelling medical devices.

EXAMPLE 1

One gram of methylmethacrylate (cement) was mixed with 0.5 ml of sterile $H_2O$ and one of the following:
1. 60 mg of minocycline
2. 60 mg of vancomycin
3. 60 mg of novobiocin
4. 30 mg of rifampin
5. 30 mg of rifampin and 60 mg of minocycline
6. 30 mg of rifampin and 60 mg of vancomycin
7. 30 mg of rifampin and 60 mg of novobiocin Equal amounts of cement alone or with antibiotics were put in the lumen of catheter latex segments in a specimen plug of the Modified Robbin's Device. Twenty-four hours later, a one-liter infusate bag made of 5% dextrose in water was infected with 5 ml of $10^5$ to $10^8$ colony forming units (CFU) per ml of slime producing *Staphylococcus epidermidis* or *Staphylococcus aureus* strains obtained from the bloodstream of patients with catheter related bacteremia. Using a peristaltic pump, the infected infusate was run for two hours at a rate of 60 ml/hr through the catheter segments of the Modified Robbin's Device.

Each catheter segment was made of 30 mm$^2$ silicone with a lumen filled with cement. At the end of two hours, some catheter segments (control and antibiotics coated) were taken out from specimen plugs and the cement in the lumen was removed, then the surface that was exposed to the infected fluid was cultured semi-quantitatively using the roll-plate technique. Other segments were left behind and flushed with saline solution for 1-4 hours, then cultured by roll-plate.

Electron microscopy was used to document the adherence of staphylococci and the formation of biofilm layer on the surface of control uncoated catheter segments. Leaching of antibiotics from the cement was demonstrated to occur for at least one week by determining the inhibition around disc-shaped pieces of cement placed on blood agar plates that had been inoculated with bacteria. Coating of the catheter segments with antibiotics was demonstrated by the zone of inhibition that continued to form for at least one week around the disc-shaped catheter segments (without cement) placed on agar plates that had been inoculated with bacteria.

These are some of the data:

| Coated Antibiotic | No. Colonies of *S. epidermis* from 30 mm$^2$ Catheter Surface | | No. Colonies of *S. aureus* from 30 mm$^2$ Catheter Surface | |
| --- | --- | --- | --- | --- |
| | Before Flush | After Flush | Before Flush | After Flush |
| Control | 522 | 329 | 138 | 7 |
| Minocycline | 239 | 70 | 18 | 0 |
| Rifampin | 417 | 1 | 27 | 0 |
| Minocycline + Rifampin | 0 | 0 | 2 | 0 |

These experiments were repeated several times and results were always consistent in showing the best results with the above combination.

EXAMPLE 2

To date, vancomycin is the only approved drug currently used to treat infections with methicillin-resistant *S. epidermidis* and methicillin-resistant *S. aureus*. Using the same general protocol as described in EXAMPLE 1, the combination of minocycline and rifampicin was found to be superior than vancomycin or a combination of vancomycin and rifampin. Following the exposure of catheter segments coated with different antibiotic combinations to an infusate infected with 5 ml of $10^3$ CFU/ml of slime producing *S. epidermidis*, the following results were obtained:

| Coating antimicrobial | Total # of colonies from 2 cm catheter segment | Adherent colonies per 2 cm catheter segment |
| --- | --- | --- |
| Control (no antibiotic) | 130 | 24 |
| Vancomycin | 176 | 17 |
| Vancomycin and Rifampin | 58 | 7 |
| Minocycline and Rifampin | 0 | 0 |

EXAMPLE 3

When all antibiotics (minocycline, novobiocin, rifampin, vancomycin) were compared alone or in combination in parallel simultaneous experiments conducted according to the protocol described in EXAMPLE 1, the following results were obtained:

| Coated Antibiotic | No. Colonies of *S. epidermis* from 30 mm$^2$ Catheter Surface | |
| --- | --- | --- |
| | Before Flush | After Flush |
| Control | 336 | 128 |
| Vancomycin | 174 | 111 |
| Novobiocin | 137 | 195 |
| Minocycline | 48 | 15 |
| Rifampin | 28 | 25 |
| Vancomycin + Rifampin | 67 | 4 |
| Novobiocin + Rifampin | 5 | 0 |
| Minocycline + Rifampin | 0 | 0 |

The combination of minocycline and rifampin and the combination of rifampin and novobiocin fulfilled all the qualifying conditions outlined below.

1. Efficacy—minocycline and rifampin were found to be active against the most resistant clinical strains causing catheter-related sepsis isolated at our medical centers. On catheter surfaces, both the combination of rifampin and minocycline and the combination of rifampin and novobiocin were very effective in preventing staphylococcal colonization. These combinations were equally effective against adherent and free floating organisms and were superior to vancomycin alone or the combination of vancomycin and rifampin.
2. Safety—the three antibiotics, rifampin, minocycline and novobiocin, have been used independently for years orally and intravenously without any significant adverse effects.
3. Bactericidal effect—both the combination of rifampin and minocycline and the combination of rifampin and novobiocin offer a rapid bactericidal effect against organisms that tend to adhere to catheter surfaces, with significant killing occuring within four hours after exposure to infected solution.
4. Resistant organisms developed to rifampin if used alone, but the drugs, minocycline and rifampin or novobiocin and rifampin, used in combination prevented the development of resistant strains.
5. This combination of minocycline and rifampin also exhibited some activity against Candida spp.
6. The combination of minocycline and rifampin and the combination of rifampin and novobiocin are synergistic in their killing activity against staphylococci adhering to catheter surfaces.

EXAMPLE 4

A combination of minocycline hydrochloride (Minocin TM, Lederle Laboratories, Carolina, Puerto Rico) and rifampin (Rifadin TM, Merrill Dow Pharmaceuticals, Cincinnati, Ohio) in a catheter flush solution was tested for stability using a formazin-standardized color-correcting Turbidimeter (Hach Ratio Turbidimeter X/R, Hach Company, Loveland, CO.) Each vial of minocycline hydrochloride and rifampin was reconstituted according to label directions using sterile water for injection. For the catheter flush solution, a final concentration of 0.1 mg/mL for each drug was prepared using 0.9% Sodium Chloride Injection, USP, as the diluent. The fully-mixed catheter flush solution was sub-divided into 20 ml portions placed into 30 ml vials. Triplicate test solutions were stored at 37°, 24° and 4° C. Aliquots were removed from each container initially and after four, eight, and 24 hours, and after three, five, and seven days and stored in two ml sterile vials at −70° C. until they were analyzed. Preliminary studies showed that −70° C. storage did not adversely affect the activity of samples.

The combination of minocycline hydrochloride and rifampin 0.1 mg/mL of each in 0.9% Sodium Chloride Injection, USP, stored at 4° and 24° C. did not result in turbidity or the development of particulates in excess of either drug separately. At 37° C., the catheter flush solution remained clear through 24 hours but in three days had developed increased turbidity that could be seen using high-intensity illumination and was measured by the turbidimeter but could not be seen in normal room light. A color change from the initial orange to a brownish-orange occurred within four hours at 37° and 24° C. and within eight hours at 4° C.

Accordingly, advanced preparation of this catheter flush solution should be limited to a maximum of three days with refrigerated storage.

Numerous modifications and variations of practicing the present invention are possible in light of the above teachings and therefore fall within the scope of the following claims.

What is claimed is:

1. An implantable medical device having one or more of its surfaces coated with an antibiotic composition comprising a combination of rifampin and minocycline, said combination coated in an amount effective to inhibit the growth of Staphylococcus.

2. The device of claim 1 wherein the combination of rifampin and minocycline is ionically bound to the surfaces.

3. The device of claim 1 wherein the combination of rifampin and minocycline is passively adsorbed to the surfaces.

4. The device of claim 1 wherein the combination of rifampin and minocycline is dispersed in a polymeric base material disposed on the surfaces.

5. An implantable medical device having one or more of its surfaces coated with an antibiotic composition comprising a combination of rifampin and novobiocin, said combination coated in an amount effective to inhibit the growth of Staphylococcus.

6. The device of claim 5 wherein the combination of rifampin and novobiocin is ionically bound to the surfaces.

7. The device of claim 5 wherein the combination of rifampin and novobiocin is passively adsorbed to the surfaces.

8. The device of claim 5 wherein the combination of rifampin and novobiocin is dispersed in a polymeric base material disposed on the surfaces.

9. A method for inhibiting staphylococcus microbial growth on surfaces of an implantable medical device comprising:
  applying to a surface of the medical device a coating of an antibiotic composition comprising a combination of rifampin and minocycline in a concentration effective to inhibit Staphylococcus microbial growth on the coated surface.

10. A method for inhibiting Staphylococcus microbial growth on surfaces of an implantable medical device comprising:
  applying to a surface of the medical device a coating of an antibiotic composition comprising a combination of rifampin and novobiocin in a concentration effective to inhibit Staphylococcus microbial growth on the coated surface.

11. The method of claim 9 where the Staphylococcus is *Staphylococcus aureus* or *Staphylococcus epidermidis*.

12. The method of claim 10 wherein the Staphylococcus is *Staphylococcus aureus* or *Staphylococcus epidermidis*.

* * * * *